US009636521B2

(12) United States Patent
Isserow et al.

(10) Patent No.: US 9,636,521 B2
(45) Date of Patent: May 2, 2017

(54) HEAT AND LIGHT TREATMENT DEVICE USING NANOTECHNOLOGY

(71) Applicants: Jonathan Isserow, Basking Ridge, NJ (US); Laura Isserow, Basking Ridge, NJ (US)

(72) Inventors: Jonathan Isserow, Basking Ridge, NJ (US); Laura Isserow, Basking Ridge, NJ (US)

( * ) Notice: Subject to any disclaimer, the term of this patent is extended or adjusted under 35 U.S.C. 154(b) by 164 days.

(21) Appl. No.: 13/940,307

(22) Filed: Jul. 12, 2013

(65) Prior Publication Data
US 2015/0013214 A1    Jan. 15, 2015

(51) Int. Cl.
*A61N 5/06*       (2006.01)
*A61F 7/00*       (2006.01)

(52) U.S. Cl.
CPC .............. *A61N 5/062* (2013.01); *A61F 7/007* (2013.01); *A61N 5/0616* (2013.01); *A61N 5/0625* (2013.01); *A61F 2007/0078* (2013.01); *A61N 2005/0647* (2013.01)

(58) Field of Classification Search
CPC .............................................. A61F 2007/0226
See application file for complete search history.

(56) References Cited

U.S. PATENT DOCUMENTS

| 5,658,583 | A  | 8/1997  | Zhang et al.   |
| 6,205,016 | B1 | 3/2001  | Niu            |
| 6,414,836 | B1 | 7/2002  | Tennent et al. |
| 6,586,133 | B1 | 7/2003  | Teeters et al. |
| 6,665,169 | B2 | 12/2003 | Tennent et al. |
| 7,116,546 | B2 | 10/2006 | Chow et al.    |

(Continued)

FOREIGN PATENT DOCUMENTS

| GB | 2515010 A | * 12/2014 |
| WO | 2010123528 | 10/2010 |

(Continued)

OTHER PUBLICATIONS

Using Freezing Conditions to Kill Bed Bugs, webpage from https://web.archive.org/web/20121115090510/http://www.bedbugs.umn.edu/bed-bug-control-in-residences/using-freezing-temperatures-for-bedbug-control, University of Minnesota (Nov. 15, 2012).*

(Continued)

*Primary Examiner* — Joseph Stoklosa
*Assistant Examiner* — Nicole L Pobre
(74) *Attorney, Agent, or Firm* — Gearhart Law LLC (57) ABSTRACT

The current invention discloses a treatment device having a heat source, a power source, a heat applicator and a lighting mechanism. The power source includes at least one nanotech battery, ensuring superior properties such as prolonged electricity production and prompt recharging. The heat applicator includes a heat conductive layer made from nanofibers, providing highly efficient heat distribution to the targeted regions. The lighting mechanism employs light emitting nano fibers to treat targeted regions. The power source provides energy to the heat and light source, which generates heat and light so that the applicator may distribute to an injury site or wound bed of a user. The current device may also be used for cooling, instead of heating applications. In addition to the medical utilizations, the current device may also play a central role in other apparatus that require thermal control capabilities.

17 Claims, 2 Drawing Sheets

(56) References Cited

U.S. PATENT DOCUMENTS

| | | |
|---|---|---|
| 7,579,077 B2 | 8/2009 | Dubrow et al. |
| 7,789,930 B2 | 9/2010 | Ensor et al. |
| 7,972,616 B2 | 7/2011 | Dubrow et al. |
| 8,025,960 B2 | 9/2011 | Dubrow et al. |
| 8,057,841 B2 | 11/2011 | Reneker et al. |
| 8,133,264 B1* | 3/2012 | LaFontaine ............ 607/112 |
| 8,269,058 B2 | 9/2012 | McCarthy et al. |
| 8,664,572 B2 | 3/2014 | Bridges |
| 2002/0026226 A1 | 2/2002 | Ein |
| 2005/0028806 A1* | 2/2005 | Kumamoto et al. ..... 126/263.02 |
| 2006/0142816 A1 | 6/2006 | Fruitman |
| 2006/0204738 A1 | 9/2006 | Dubrow et al. |
| 2006/0282134 A1* | 12/2006 | Shapiro et al. ............ 607/88 |
| 2008/0015665 A1* | 1/2008 | Lachenbruch ........... A61F 7/10 607/104 |
| 2008/0023394 A1 | 1/2008 | Naruse et al. |
| 2008/0069848 A1 | 3/2008 | Peters |
| 2008/0069905 A1 | 3/2008 | Peters |
| 2008/0071206 A1 | 3/2008 | Peters |
| 2008/0109941 A1* | 5/2008 | Moreshead ............... 2/243.1 |
| 2008/0141681 A1* | 6/2008 | Arnold ..................... 62/3.5 |
| 2008/0170982 A1* | 7/2008 | Zhang ................... B82Y 10/00 423/447.3 |
| 2008/0294161 A1 | 11/2008 | Wolf, Jr. et al. |
| 2009/0163984 A1 | 6/2009 | Robinson et al. |
| 2010/0021819 A1 | 1/2010 | Zhamu et al. |
| 2010/0280584 A1 | 11/2010 | Johnson et al. |
| 2010/0285972 A1 | 11/2010 | Dubrow et al. |
| 2011/0064785 A1 | 3/2011 | Daniels et al. |
| 2011/0152643 A1 | 6/2011 | Xue et al. |
| 2011/0170236 A1 | 7/2011 | Young |
| 2011/0178574 A1 | 7/2011 | Hardy et al. |
| 2011/0178585 A1* | 7/2011 | Biser ...................... A61F 7/02 607/109 |
| 2011/0201984 A1 | 8/2011 | Dubrow et al. |
| 2011/0218601 A1* | 9/2011 | Uchiyama ................ 607/112 |
| 2011/0309774 A1 | 12/2011 | Peng et al. |
| 2012/0022620 A1* | 1/2012 | Khodak et al. ........... 607/96 |
| 2012/0130459 A1 | 5/2012 | Kim et al. |
| 2012/0157904 A1 | 6/2012 | Stein |
| 2012/0256704 A1 | 10/2012 | Johnson et al. |
| 2013/0096518 A1 | 4/2013 | Hall et al. |
| 2013/0176699 A1 | 7/2013 | Tonchev et al. |
| 2014/0031748 A1* | 1/2014 | Usui ...................... A61F 7/03 604/113 |
| 2014/0206947 A1* | 7/2014 | Isserow et al. ............ 600/301 |
| 2014/0207212 A1* | 7/2014 | Isserow et al. ............ 607/89 |
| 2014/0207216 A1* | 7/2014 | Isserow et al. ............ 607/96 |
| 2014/0288624 A1* | 9/2014 | Wasko et al. ............ 607/109 |
| 2014/0318699 A1 | 10/2014 | Loginotti-Buitoni et al. |
| 2014/0364778 A1* | 12/2014 | Leftly ................. A61N 5/0613 601/18 |
| 2015/0119849 A1* | 4/2015 | Aronhalt ............... A61F 7/10 604/506 |

FOREIGN PATENT DOCUMENTS

| | | |
|---|---|---|
| WO | WO 2010123528 A2 | 10/2010 |
| WO | WO 2010123528 A3 | 10/2010 |
| WO | 2011112364 | 9/2011 |
| WO | WO 2011112364 A1 | 9/2011 |

OTHER PUBLICATIONS

Expert Witness/Entomology, webpage from https://web.archive.org/web/20120531100823/http://insectexpertphd.com/mites.aspx, (May 31, 2012).*

Izri A. and Chosidow, O. Efficacy of Machine Laundering to Eradicate Head Lice: Recommendations to Decontaminate Washable Clothes, Linens, and Fomites. Jan. 15, 2006, Clinical Infectious Diseases, 42:e9-10.*

Berger, Michael. "Light-emitting nanofibers shine the way for optoelectronic textiles". Jan. 27, 2012, Nanowerk. http://www.nanowerk.com/spotlight/spotid=24096.php.*

Joo, Yeail, et al; Characterization of a new acne vulgaris treatment device combining light and thermal treatment methods; Skin Res Technol. Feb. 18, 2012, (1): 15-21; Published online May May 18, 2011. doi: 10.1111/j.1600-0846.2011.00540.x.

Ruetzler, Kurt, M.D., et al; Forced-Air and a Novel Patient-Warming System (vitalHEAT vH2) Comparably Maintain Normothermia During Open Abdominal Surgery; www.anesthesia-analgesia.org; Mar. 2011; vol. 112; No. 3; pp. 608-614.

Babilas, Philipp, M.D.; Intense Pulsed Light (IPL): A Review; Lasers in Surgery and Medicaine 42:93-104 (2010).

Wainwright, Mark, Photodynamic Antimicrobial Chemotherapy (PACT), Journal of Antimicrobial Chemotherapy, 1998, pp. 13-28, vol. 42, The British Society for Antimicrobial Chemotherapy.

Suh, HJ, et al., The Combined Effect of a Three-Channel Electrode Delivery System with Local Heat on the Healing of Chronic Wounds., Diabetes Technol Ther., Oct. 2009, pp. 681-688.

Kelkarr S.S., et al., Theranostics: combining imaging and therapy., Bioconjug Chem. Oct. 19, 2011, pp. 1879-1903. Epub Aug. 29, 2011, http://www.ncbi.nlm.nih.gov/pubmed/21830812.

International Search Report for PCT Application No. PCT/US/2014/012249. Mailed Jun. 10, 2014. 7 pages.

Cole, Gary W., MD.; Photodynamic Therapy; MedicineNet..com; www.medicinenet.com/photodynamic_therapy/page12.htm (Jul. 10, 2013).

Radiancy, Inc. No!no! Skin. webpage from https://www.nonoskin.com (Jul. 10, 2013).

* cited by examiner

HEAT AND LIGHT TREATMENT DEVICE USING NANOTECHNOLOGY

CLAIM OF PRIORITY

This application claims no priority to any U.S. patent or patent application.

FIELD OF THE INVENTION

The current invention relates to a wound, infection, or injury treatment device and related methods. In particular, by using nanotechnology enabled heating and lighting processes, the current invention relates to a device and methods that may be used for treatment of a wound, injury, skin infection such as acne, ailment, or disease, as well as the pre-treatment to prevent wound infections prior to surgery and maintaining normothermia during surgery.

BACKGROUND OF THE INVENTION

Many kinds of diseases and accidents may cause harm to the human body and result in pain, wound, infection, and injury that require both swift and continuous treatments. The treatment of such wounds/injuries has been a crucial part of healthcare. Various methods and devices have been developed to improve the quality of care that may be provided in such treatments and the healing process. Among these approaches are temperature alternation techniques, such as the application of heat or coldness by different sources.

Application of heat, or coldness, or alternating temperature changes have been widely used in the treatment of wound, infection, pain, and injury for a very long time. In addition, the heating treatment may also prevent cutaneous/skin infections as well as preventing skin infection preoperatively. Heating treatments such as heat pads are believed to cause the dilation of blood vessels, facilitate perfusion to the target tissues and cycling of blood, and sterilize the targeting area. Cold treatments such as ice pads reduce swelling and are used in pain management following injury.

The temperature altering treatments, especially the application of heat, are widely in use but there are still a number of general shortcomings. For example, the heat applicators nowadays are generally bulky and difficult to fit onto small wounds or injuries at locations that are hard to access. Perioperative heat treatment, known to significantly reduce post operative wound infection, is currently not practically available because of a limitation in available devices that are portable and do not require bulky hardware for each individual patient to facilitate treatment. There is a distinct need for an easy to use portable inexpensive bandage device that can be applied periopertively to all patients that is not limited by the resource of fixed, expensive hardware. In addition, the regular heating applicators are not long lasting, requiring frequent change of the applicator. Thirdly, some of the heat applicators are hard to reheat. The ability to provide consistent thermoregulation is critical to the prevention of infection as fluxes in temperature (i.e. too hot or not hot enough) can have an adverse outcome in patient management.

In general, the existing heating application treatment devices are low in efficiency and high in waste of energy. These treatment devices cannot keep up with the development of new problems, such as the escalating crisis of multi-drug resistant infections including Methicillin-resistant *Staphylococcus aureus* (MRSA). The medical literature demonstrates significant reduction in post-operative wound infection in patients who received warming prior to surgery for a 30 minute period with reduction rates from 14% to 5%. It is critical that an easy to use device with thermoregulatory control be available to all patients undergoing surgery particularly in light of the escalating crisis of multi-drug resistant infections including Methicillin-resistant *Staphylococcus aureus* (MRSA). Therefore, the development of new technology is desirable and the current invention serves as a powerful alternative to the previous devices.

The application of light to the human body is the basis for phototherapy. These therapies have been used in the treatments of many ailments such as cancer, acne, and psoriasis. Similar to temperature therapies, the application of some lights, such as lasers, helps to promote circulation. In the same realm, are photodynamic therapies. This form of phototherapy uses a non-toxic, non-reactive substance that when exposed to select wavelengths of lighting becomes toxic and attacks the targeted cells. This is instrumental in being able to target a particular cell or area and leaving surrounding tissue unharmed. These compounds can kill many bacteria, fungi, and viruses.

However, the increasingly popular phototherapies have a number of general shortcomings as well. The current models on the market for treating acne are small and treat one pimple at a time. Depending on the person, this can end up costing them an inordinate amount of time. There are larger models on the market, however, these models are also not form fitting and require a user to simply hold the device to the affected area for the prescribed amount of time. Thus, the user must remain in a fixed position for upwards of one hour and then change the position of the device to treat another area.

Nanotechnology stands at the vanguard of integrating science and engineering and it has undergone significant progress in recent years. By using materials having nanometer level dimensions and special physical characteristics, nanotechnology has been proved to be a promising field of innovation. In particular, a number of improvements in nanotechnology using nanofibers, nanotubes, and nano-particles have enabled the production of batteries that provide higher energy density, last longer, and/or recharges faster. In addition, nanofibers have been shown to be applicable in a number of disciplines such as material science, molecular biology, and medical sciences. Nevertheless, the use of nanofibers and nanotechnology batteries in medical devices, particular treatment devices, has been scanty and leaves much to be desired. The current invention addresses the aforementioned needs.

Reviewing of Related Technology:

US20080023394 discloses a medical filter material comprising a dispersion of nanofibers of thermoplastic polymer having a number average diameter of 1 to 500 nm wherein the ratio of single fibers with a diameter of more than 500 nm and 1 nm or less is 3% or less in terms of weight ratio. Further, there are provided, utilizing the medical filter material, an extracorporeal circulation column and a blood filter. Through the employment of nanofibers small in fiber diameter dispersion, high in strength and high in productivity, there can be provided a medical filter material excellent in hemadsorption performance and protein adsorption performance. Through packing with this medical filter material, there can be provided high-performance extracorporeal circulation column and blood filter.

US20080069905 teaches a therapeutic treatment device comprising a compound comprising a drug and a nitric oxide (NO) eluting polymer arranged to contact a treatment site in or on a body. The device is acting as a booster for drug eluting patches, e.g. pharmaceuticals, vitamins, nicotin, nitroglycerin, whereby with advantage two therapeutic treatments, of significant value, are combined in one treatment. A synergetic effect is achieved by such devices because NO that is eluted from the device boosts the effect of the drug, as the treatment site is more susceptible to said drug by the effect of the eluted NO.

Various devices are known in the art. Nevertheless, their structures are distinctively different from the current invention. Moreover, the other inventions fail to address all of the problems solved by the invention described herein. One embodiment of this invention is illustrated in the accompanying drawings and will be described in more detail herein below.

SUMMARY OF THE INVENTION

The current invention discloses a treatment device, and in particular a wound/infection/injury treatment device, comprising: a heat source; a heat applicator connected to the heat source; the heat applicator comprising: a heat application layer having an application surface and a heat receiving surface, and a heat conductive layer having a front side and a back side, wherein the heat conductive layer is made of nanofibers extensively affixed to the heating receiving surface of the heat application layer; a power source connected to the heat source, empowering the heat source, the power source comprising at least one nanotech battery; and a lighting mechanism, where the lighting mechanism is woven into the heat application layer. Preferably, the power source and the heat source are integrated into a heat generating body directly attached to the back side of the heat conductive layer of the heat applicator, wherein the heat applicator is a layered flat structure, incorporating the heat application layer and the heat conductive layer.

Preferably, the heat conductive layer comprises nanofibers woven or unwoven but pressed into a layer that efficiently and extensively transfers heat to the heat application layer. Many specific nanofibers, nanofilaments or nanotubules may be used in the heat conductive layer. Preferably, the lighting mechanism comprises light emitting nanofibers. For clarity purposes, the term nanofiber is used to generally cover all the nanofibers, nanofilaments, nanotubules, and other fibrous materials having diameters preferably between 0.5 nm and 1um. Additionally, the materials may be of a micro origin of about 100 nm to 100 um in diameter.

The power source is preferably a nanotechnology battery that possesses certain superior properties compared with conventional lithium batteries. The power source may produce higher energy density. The power source may last longer than conventional batteries. The power may also be charged and recharged promptly. In particular, nanotechnology has been used to produce "supercapacitors" that may be incorporated in rechargeable batteries. Preferably, the current treatment device employs such a supercapacitor battery allowing quick recharges.

Using the device described above, the user of the device may cause thermal and luminary alternations to the injury site or wound bed, allowing faster and more complete recovery. In particular, the device may be used to apply heat to the injury site or wound bed. The device may also be used to treat infections such as bacteria infections that are susceptible to increased temperature. The specific applications of the device are extensive.

The treatment device may further comprise a control mechanism connected to the power source. The device can be remotely programmable utilizing blue tooth/smart phone technology so that a patient and/or physician could program the device remotely or wirelessly for certain predetermined cycles/temperatures/functions. The device could also provide real time feedback in terms of data including physiological as well as visual data. The control mechanism may be used to initiate, adjust, and end the application of thermal alternation (heat or coldness). With the control mechanism, the user of the treatment device may easily control the treatment process and change the durations, cycles, and intensity of the treatments.

In general, the present invention succeeds in conferring the following, and others not mentioned, desirable and useful benefits and objectives.

It is an object of the present invention to provide a treatment device that may be used to facilitate the healing of injuries, infections, acne, or wounds on humans and other subjects.

It is an object of the present invention to provide a treatment device that may cover the wound bed or injury site.

It is an object of the present invention to provide a treatment device that alters the temperature of a wound, infection or injury site.

It is an object of the present invention to provide a treatment device that applies heat to a wound or injury site.

It is an object of the present invention to provide a treatment device that is light and portable.

It is another object of the current invention to provide a treatment device that may be used for different kinds of wounds/infections/injuries.

It is another object of the current invention to provide a treatment device that may be used for wounds/injuries on different parts of a body, including musculoskeletal pain.

It is still another object of the current invention to provide a treatment device that is easily adjustable.

It is another object of the current invention to provide a treatment device that uses a supercapacitor battery that is easily rechargeable.

It is yet another object of the current invention to provide a treatment device that uses nanofibers for efficient heat conduction.

It is another object of the current invention to provide a treatment device that has an integrated body.

It is yet another object of the current invention to provide a treatment device that is easy to use and easy to manufacture.

It is an object of the present invention to provide a treatment device that uses heat energy to treat vascular ailments such as poor circulation including peripheral vascular disease and diabetes.

It is an object of the present invention to provide a treatment device that helps an individual to maintain a homeostatic temperature including maintaining normothermia and specific core temperature requirements for patients before, during, and after surgery.

It is an object of the present invention to provide a treatment device that uses light for the purpose of photodynamic therapies.

It is another object of the present invention to provide a treatment device that uses heat and or light to increase absorption and efficacy of topical medicinal applications including creams, ointments, photodynamic agents and topical antibiotics.

It is another object of the present invention to provide a treatment device that uses light for the treatment of varying skin conditions including red, green, and blue light sources.

It is another objective of the present invention to provide a treatment device that uses bipolar radio frequency and/or light energies in the removal of hair.

It is another objective of the present invention to provide intense pulsed light, laser and other light applications with specific ability to regulate dosimetry and duration of therapy as well as location (area treated) during therapy.

It is another object of the present invention to provide a treatment device that uses transcranial low level laser therapy (LLLT) in the management of traumatic brain injury and stroke, pain, symptoms related to medical conditions including rheumatoid arthritis, osteoarthritis, tendinopathy, and wound treatment.

It is an object of the present invention to provide a treatment device that can be inserted into orthopedic casts for reduced healing time and wound infection prevention and management It is another object of the present invention to provide a treatment device for the extermination and control of parasite and mite infestations including house dust mites and bed bugs in mattresses, bed linens, clothing and suitcases.

It is another object of the present invention to provide a treatment device that can be used in the treatment of parasites including lice using heat and/or light applications.

It is an object of the present invention to provide a treatment device that can be programmable directly and/or remotely utilizing blue tooth/smart phone technology so that a patient and/or physician could program the device remotely or wirelessly for certain predetermined cycles/temperatures/functions. The device could also provide real time feedback in terms of data including physiological as well as visual data.

It is another objective of the present invention to provide a treatment device that can be used for menstrual pain management with heat therapy It is another object of the present invention to provide a treatment device that can utilize a nano generator whereby mechanical movement can harvest energy utilizing piezoelectric technology by converting energy from mechanical stresses into energy properties It is another object of the present invention to provide a treatment device the can utilize nanophotonics/light-emitting nano fibers and/or photoluminescent nano fibers, nano-fibers and luminescent particles such as quantum dots (QDs).

It is another object of the present invention to provide a treatment device that facilitates light generation utilizing preferably nano components and is rechargeable and/or disposable.

It is another object of the present invention to provide a treatment device that micro components could be used if desired.

It is another object of the present invention to provide a treatment device that can be used for cooling and/or heat redistribution for computers, electronics, and air conditioners.

DESCRIPTION OF THE PREFERRED EMBODIMENTS

The preferred embodiments of the present invention will now be described with reference to the drawings. Identical elements in the various figures are identified, as far as possible, with the same reference numerals. Reference will now be made in detail to embodiments of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto without deviating from the innovative concepts of the invention.

Figure 1:
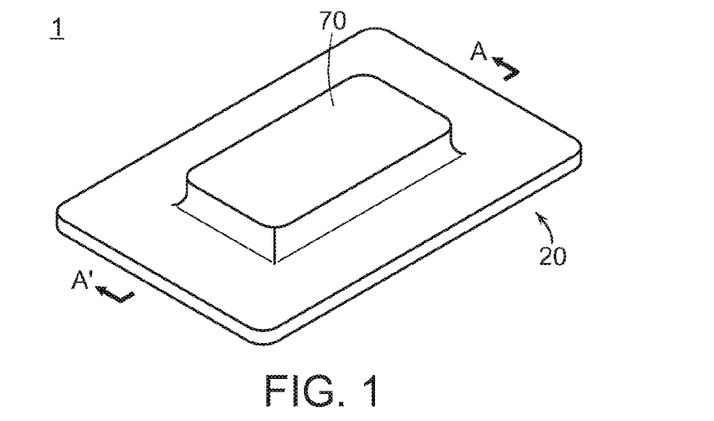
FIG. 1 shows a back perspective view of a treatment device embodying the current invention.

FIG. 1 shows a back perspective view of a treatment device embodying the current invention. Shown in FIG. 1 is the treatment device 1 having a heat generating body 70 attached to a heat applicator 20.

Figure 2:
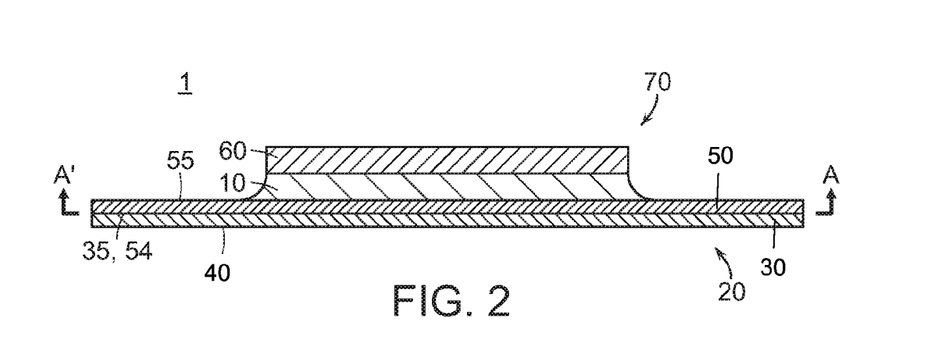
FIG. 2 shows a sectional view of the treatment device shown in FIG. 1.

FIG. 2 shows a sectional view of the treatment device shown in FIG. 1, as indicated by markers A and A'. Shown in FIG. 2 is the treatment device 1 having a heat generating body 70 attached to a heat applicator 20. The heat generating body 70 comprises a heat source 10 and a power source 60, wherein the heat source 10 and power source 60 are preferably connected by wires (not shown). In addition, the heat applicator 20 comprises a heat application layer 30 and a heat conductive layer 50, wherein the heat application layer 30 has a heat receiving surface 35 and a heat application surface 40, and the heat conductive layer 50 has a front side 54 and a back side 55. The heat application surface 40 has a lighting mechanism 75 (see FIG. 3). Preferably, this lighting mechanism manifests itself as a light emitting nano fiber woven into the heat application surface 40. The front side 54 of the heat conductive layer 50 directly engages with the heat receiving surface 35 of the heat application layer 30. The heat application surface 40 is designed to engage exposed human wound beds or injury sites.

Figure 3:
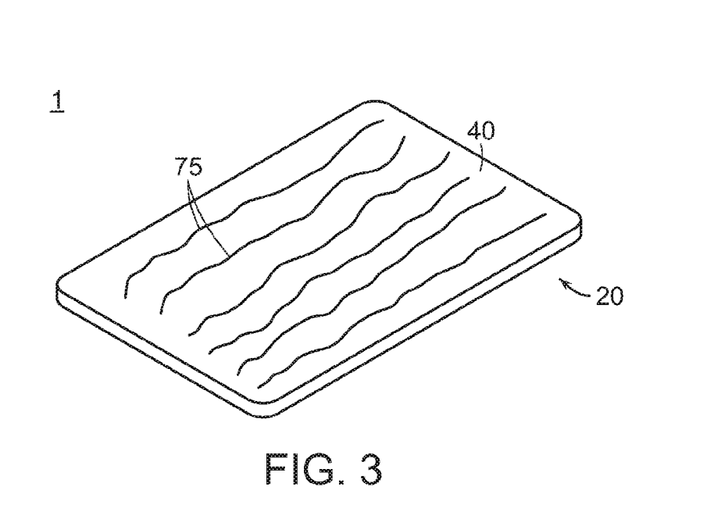
FIG. 3 shows a front perspective view of the treatment device.

FIG. 3 shows a front perspective view of the treatment device 1. Shown in FIG. 3 is the heat application surface 40 with the integrated lighting mechanism 75 of the heat application layer 30, which is part of the heat applicator 20.

Figure 4A:
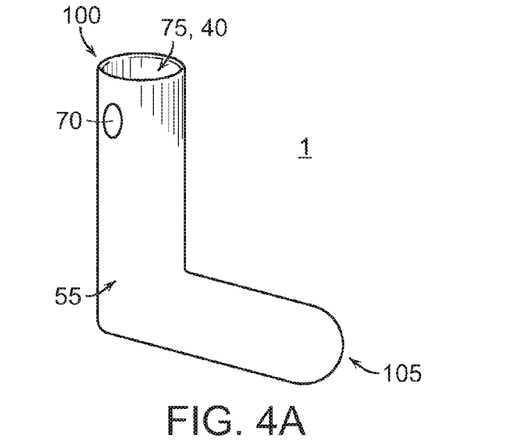
FIG. 4A shows an illustration of an alternate embodiment of the treatment device as an arm sleeve.

FIGS. 4A, 4B, 4C and 4D display alternate embodiments of the current invention. In FIG. 4A, the current invention is shown as a stocking for a leg. The individual slides their leg into the void 100 until their toes are resting comfortably in the terminal end 105 at the base of the device 1. The heat generating body 70 is placed on the back surface 55 of the device 1. The heat generating body 70 may be placed in alternate areas as to provide the most comfortable access to the device. The stocking may include toe slots, similar to toe socks, rather than a uniform base. This would provide more surface area for the heat and light to treat.

Figure 4B:
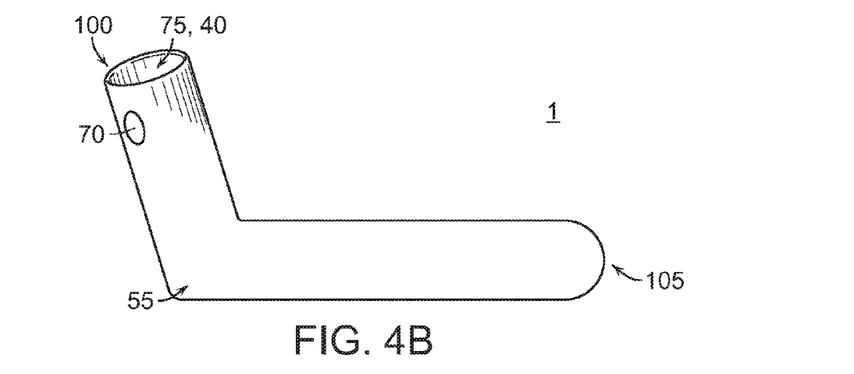
FIG. 4B shows an illustration of an alternate embodiment of the treatment device as a leg sleeve.

In FIG. 4B, the device 1 is shown as a stocking for an arm. Again, a user slides their arm into the void 100 and to the terminal end 105 at base of the stocking. The heat generating body 70 is positioned on the back surface 55 of the device 1. Alternatively, the heat generating body 70 may be positioned to best provide user access and manipulation. The stocking may include finger slots, like a mitten, to provide an increased surface area for the heat and light to treat.

Alternatively, the device 1 comprising the stocking may be of differing sizes and have Velcro® hook and loop fasteners, or another adhesive means, to wrap and secure the apparatus to the affected limb. The stocking may also have a preformed shape (to fit an extremity) with openings disposed at each end. Thus, this would be a more traditional sleeve rather than a stocking and provide a greater range of mobility. Such varying embodiments would be most beneficial to those that are afflicted by diabetes, vascular diseases, and the like. These individuals typically have poor circulation that sometimes requires amputation of the affected appendage. The increased heat focused on these areas promotes increased blood flow and anti-inflammatory qualities, which, in turn, may aid in the prevention of such drastic measures from being taken. Additionally, the increased blood flow can increase nitric oxide (NO) production and delivery. Nitric oxide is a vasodilator and thus can have a synergetic effect along with the heat treatment. Thus, with the aid of this device 1 increased NO production can be done by taking advantage of physiological mechanisms rather than by employing expensive pharmaceuticals.

Figure 4C:
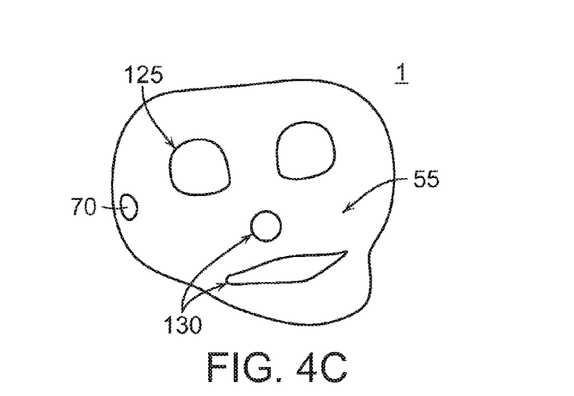
FIG. 4C shows an illustration of an alternate embodiment of the treatment device as a mask.

In FIG. 4C, the treatment device 1 takes the form of a mask. The mask has protective eye slits 125. These protective eye slits 125 remove heat and/or light from the area and protect the eye from any harm stemming from the treatments. The protective eye slits 125 may also have built-in protective coverings for the eyes, similar to goggles, to generally protect the eyes from harm related to usage of the device 1. The wavelengths typically used with the treatment of some skin ailments (blue and red) can damage the retina of the eye without proper protection. The mask also provides for breathing slits 130 as well to aid in the comfort of the wearer.

Figure 4D:
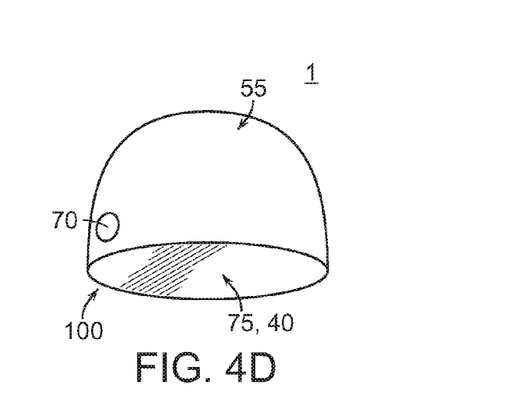
FIG. 4D shows an illustration of an alternate embodiment of the treatment device as a wearable cap.

In FIG. 4D, the treatment device 1 takes the form of a wearable cap or head covering. The cap may come in variable sizes or have the ability to conform to the user's head. The user puts the device 1 onto their head by placing their head in the void 100 until the top of their head touches the heat application surface 40. From there, the heat generating body 70 provides the heat desired by the user. The heat generating body 70 is on a back surface 55 of the device 1. This embodiment is key in fighting various afflictions centered on the head of the user. For instance, lice and bed bugs are both susceptible to heat. Heat treatments can be used to help rid an individual of these parasites.

FIGS. 1, 2, 3, 4A, 4B, 4C and 4D show various embodiments of the current invention. However, it should be noted that the design of the current invention may vary significantly from the embodiments described herein. As long as the general inventive spirit stays consistent with the disclosure, the variations of embodiments should be considered part of the current invention. While some of the variations are hereby described, the other variations may be considered general knowledge to a person skilled in the art so that they do not required detailed discussion. The teachings and disclosures of the current invention encompass all the variations.

The power source 60 of the current invention may employ any kind of electricity generating or storing devices. Preferably, the power source here is a rechargeable battery using nanotechnology. For example, the nanotech battery may use silicon nanowires on stainless steel substrate, providing 10 times the power density of conventional lithium ion batteries. Alternatively, the nanotech battery may use aligned carbon nanotubes on a substrate to establish the anode or cathode in a conventional battery, improving the power generating capacity by almost 10 fold. More preferably, the power source is a battery utilizing nanotech supercapacitor technology, which can be recharged promptly. For instance, by using graphene on the surface of anodes to make lithium-ion batteries, the batteries may be recharged 10 times faster than common rechargeable batteries. The fast recharging nanotech batteries are particularly suitable as the power source 60 herein included in the current invention. With such designs, the treatment device may be used more widely in emergency situations because the initiation of treatment and alternation of devices may become more time-saving and efficient.

In addition to the technologies described above, the power source 60 may also use other nanotechnology, such as but not limited to: lithium sulfur batteries (using carbon nanofibers encapsulating the sulfur in the cathode or using mesoporous carbon nanoparticles that embraces sulfur inside the nanopores of the cathodes), nanocomposite batteries (using cathodes made of a nanocomposite designed to increase the energy density of the Li-ion batteries), nanostructured lithium titanate battery having enhancing charge/discharge capability, fast charge/recharge batteries using silicon nanoparticles coating a titanium disilicide lattice, thermocells using nanotubes that generate electricity, electrical generator built with nanostructured material that can generate electrical power from the user's body motion such as walking, and ultracapacitor batteries using single atom thick graphene sheets, and any combinations of batteries and power sources thereof.

Besides incorporating nanotechnology batteries, the power source 60 may also utilize other readily available supplies of electricity. For example, the power source 60 may be a power cord and power plug that can be directly connected to a common alternating current electricity outlet. Alternatively, the power source 60 may be a regular battery or battery pack, either rechargeable or non-rechargeable. The battery may be a regular AAA zinc-carbon or alkaline battery, or any other type or size that may fit the energy needs and/or physical accommodations of the current treatment device. Alternatively, the power source 60 may be a nano generator. The nano generator may have a piezoelectric property that allows energy harvesting from mechanical stresses. Such an option would allow for the operation of the device 1 without a battery. However, it may be practical to employ a back-up battery in case of generator failure.

The heat source 10 is used to produce heat from the electricity generated by the power source 60. The design of the heat source 10 is generally known in the art and it may vary according to the characteristics of the electricity produced by the power source 60 and the specific requirements of the user and the injury/wound/infection to be treated. The heat source 10 may be a separate structure from the power source 60, or on the alternative, a part of an integrated structure, such as a heat generating body 70, which also includes the power source 60. The connection between the heat source 10 and the power source 60 may vary as well. In an alternative embodiment, the heat source 10 is removably attached to the power source 60, wherein after the heat source is considered to have produced enough heat, the power source 60 is detached from the heat source 10 and the rest of the treatment device 1, which is used to treat the wound bed or injury site, reducing the weight the treatment device and allowing the user of the treatment device to move around more freely. In another embodiment, the power source 60 may be connected to a plurality of heat sources 20 by long wires to ensure continued power supply to a number of treatment devices.

The heat applicator 20 is designed to apply the heat produced by the heat source 10 to the user of the treatment device. The heat applicator 20 in the current embodiment has a heat application layer 30 and a heat conductive layer 50. However, it should be noted that the heat application layer 30 and the heat conductive layer 50 may be a single layer integrated together and having both heat application and heat conducting capabilities. As to the embodiment shown in FIG. 2, the heat conductive layer may be made from woven or unwoven nanofibers that are extensively affixed to the back side of the heat application layer 30. The nanofibers used in the heat conductive layer 50 may include but not limited to: inorganic nanofibers such as ceramic nanofibers made from titanium dioxide ($TiO_2$), silicon dioxide ($SiO_2$), zirconium dioxide ($ZrO_2$), aluminum oxide ($Al_2O_3$), lithium titanate ($Li_4Ti_5O_{12}$), and titanium nitride (TiN) or platinum (Pt), organic or polymer nanofibers such as but not limited to polystyrene, polyacrylonitrile, polycarbonate, PEO, PET and water-soluble polymer nanofibers, and bi-component nanofibers, and any combinations thereof. The key property of the nanofibers making up the heat conductive layer 50 is that the nanofibers are capable of efficient transferring and distribution of heat. For example, the thermally treated carbon nanofibers produced by Aldrich (Pro. No. 719781) may be used for the heat conductive layer 50. In addition, the nanofibers of the heat conductive layer 50 may be capable of prolonged and controlled distribution of heat.

The heat application layer 30 is preferably made from thin and absorbent material so that it may evenly distribute the heat generated by the heat source to the wound bed or injury site and it may absorb the exudates, if any is produced by the wound or injury. As indicated above, the heat application layer 30 may be integrated with the heat conductive layer 50, forming a single layer. Thus, the materials usable for the heat conductive layer 50, as indicated above, may also be utilized for the heat application layer 30. In addition, the heat application layer 30 may be made from materials such as but not limited to: woven or unwoven fabric, cloth, terrycloth, woven or woven fibers of wool, flax, cotton, and/or yarn, mineral textiles such as but not limited to asbestos, glass and/or fiberglass, and synthetic textile including but not limited to nylon, polyester, and/or acrylic, or any combinations thereof. The heat application layer 30 may have a heat application surface 40, which may be sticky or have a sticky edge to ensure covering or partial covering of the wound, infection or injury. The treatment device 1, in its unused form, may further include a non-sticky layer attached to the heat application surface 40. The non-sticky layer may be removed before use, allowing the treatment device to be securely attached.

The lighting mechanism 75 is preferably a light emitting nanofiber layer woven into the heat application surface 40. Further, photoluminescent nanofibers may be employed. By taking optical nanofibers and combining them with quantum dots, one can produce a wide spectrum of lighting options and applications. The advantage to using these light emitting nanofibers manifests itself in high efficiency lighting with reduced power consumption. When done correctly, this produces quantum efficiencies in the range of 0.65 to 0.95. Additionally, these nanofibers provide flexible lighting options. They can be woven and bent into various shapes and fabrics of varying strengths.

In the current embodiments as shown in FIGS. 1, 2 and 3 the heat applicator 20 and heat generating body 70 are both shown as having a rectangular shape. It should be noted that the shape and size of the heat applicator 20 and the heat generating body 70, as well as various components of the treatment device 1, may vary according to the specific design of the device, the need of the user and the wound/infection/injury to be treated. The device and its components may take any shape also due to the extensive use of the current invention such as FIGS. 4A, 4B and 4C. As indicated below, the device herein disclosed may also utilize in applications that generally require thermal control. For example, the device may be made into pads, strips, or even clothing, in order to satisfy the specific need of the application. The size of the applicator may range from 1 $mm^2$ to 10 $m^2$, with the preferred range of 10 $mm^2$ to 100 $cm^2$. The weight of the treatment device 1 is preferable light, ranging from 0.1 g to 10 kg, and a preferred range of 1 g to 1 kg. The components of the device are preferably removably attached so that each part may be detached from the others and used separately. The applicator portion of the device may be cut or divided into intended size and shape to ensure convenient application.

Instead of a heat source 10, as indicated above, the treatment device 1 may include a refrigerating unit to make the treatment device capable of reducing temperature. Such an alternation allows the treatment device to be used similar as a cold pack, which may stabilize some injuries/wounds and facilitate recovery.

The current treatment device may be used for any kind of wounds, infections, injuries, and ailments. In addition, the current device may also be used to prevent wound infection by heating a target area prior to surgery. The basic function of the treatment device is to alter the temperature of an external injury site or wound bed to enhance healing and facilitate recovery. In addition, the current treatment device may be used for pain management, mainly by promoting blood flow and improving recovery. The current device may also be used to apply heat treatment for acne and other skin disorders, such as warts, psoriasis, eczema and cancer. In organ transplantation, this device may be used to control and maintain the temperature of the transplant organs during transportation and storage of the transplant organs, as the organs require specific temperature control.

Those skilled in the art will appreciate that the light and/or heat treatment therapies can be used to treat a range of skin conditions including acne, warts, psoriasis, eczema and cancer as well as many other afflictions. The light or heat treatment may also treat a number of subcutaneous afflictions such as muscle and nerve regeneration, promoting bone healing and managing pain associated with various diseases.

In some embodiments, the lighting mechanism can vary depending on the specific treatment desired. This means the lighting element 75 may be a number of different means including light emitting diodes (LEDs), lasers, and ultraviolet (UV) light amongst others. The particular lighting element 75 may change to reflect a specific intended use. Photodynamic medications are activated by a lighting element 75 after a predetermined incubation period. The incubation period varies by the medication, but in any event is the time from which the medicine is ingested or applied until the time the lighting element 75 is applied to the targeted area. Drugs used in such treatments may include Photofrin®, Levulan®, and Metvix® which are used for the treatment of certain cancers.

Skin afflictions such as acne can be treated by lasers, LEDs or both. The types of lasers employed by the device for this type of treatment may include Diode, Pulsed Dye, Fractional, KTP, Infrared, and Pulsed Light and Heat Energy (LHE) lasers. In the alternative, the lighting element 75 may consist of a plurality of LEDs affixed or interwoven into the heat application surface 40. The LEDs may also be present in the treatment device 1 itself and shine through one or more layers of the device. In treating acne, blue wavelength light is typically used for effective treatments. However, the combination of blue wavelength and red wavelength light is sometimes used in conjunction with one another. The duration of the treatment varies between individuals and their particular skin types and conditions, but can range from 10 minutes up to 1 hour.

Additionally, ultraviolet light may be used to treat certain skin conditions such as psoriasis. Preferably, the UV-B spectrum of light would be used for this purpose. UV-A light can be used for such a treatment, but must be used in conjunction with a light sensitizing medication. Such medications can be taken either topically or orally and will allow the UV-A light to be effective for treatment purposes. If one desired to employ lasers for treating psoriasis, an example might be an Excimer laser or Pulsed Dye laser. Radiofrequency may also be employed for various skin therapies and epilation.

Another practical use of the treatment device 1 combines the heating properties with the use of topical therapeutics such as various types of pain medications or antibiotics. The device 1 may be applied to a particular area in order to increase the uptake of a particular topical drug or antibiotic. The topical drug is applied to the surface of the skin, and then the device 1 can subsequently be applied to the same area. The process is the same if the medication is not topical but rather taken internally. The treatment device 1 in this instance may take any shape as necessary for the intended functionality. There are a number of drugs whose interaction with light can create unwanted side effects including redness, folliculitis, and darkening or lightening of the skin. Thus, in some embodiments, one may desire to use only the heat source and not the light source. These embodiments may provide for a switch or means for turning the light source on or off. By using only the heating source 10 of the device 1, one can avoid any potential side effects of limitations of using the lighting element of the device 1. Again, the treatment device can be formed to fit a number of different bodily structures, which includes but is not limited to masks, bandages, stockings, sleeves, and patches.

Beside its medical applications, the current device may also be used as other heating or cooling apparatus, such as but not limited to clothing apparel and accessories including gloves/hand warmers, jackets, pants, socks, shoe insert, ear muffs, footwear such as ski boots, and winter boots, ski equipment, goggles, ice skates, seat pads, portable seat cushions, and heatable or coolable containers. In particular, the device may be incorporated into mattress, bed cushions, mattress covers, comforters, pillows, and bed linens, etc., for the treatment of bed bugs, house dust mites and other parasitic infestations such as lice. The device can be incorporated into a head covering for treatment of lice, bed bugs and the like as they are sensitive to increased temperature. A thermal cover could also be used to encase an entire mattress and or bed. Alternatively, the current nanotech heating device may be included in a thermal bag, which may be used in the management of bed bugs by treating bed linens, comforters, pillows, as well as clothes. In addition, the fast-charging and long-lasting nature of the current device allows the device to be included a thermal blanket. The thermal blanket may be used for the treatment of hypothermia and the treatment of cardiac arrest with medically induced hypothermia. As long as the apparatus requires thermal control capability, the current invention may play a central role.

As indicated above, the treatment device may further comprise a control mechanism connected to the power source. The control mechanism may be used to initiate, terminate, and adjust the electricity provided by the power source, thus controlling thermal alternation capability of the device. With the control mechanism, the user of the treatment device may easily control the treatment process and change the durations, cycles, and intensity of the treatments. Additionally, the control mechanism may not be directly connected to the power source. In this instance, the control mechanism is a wireless device capable of communicating with the device 1 itself. Preferably, a user can employ a Bluetooth® enabled device (i.e. smart phone) to change particular settings such as temperature, cycles, light intensity and a variety of other functions by way of mobile application. This embodiment may also allow for the real time monitoring of the device 1 and permit the device 1 to send physiological data to the user (i.e. a doctor) in real time.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A treatment device, comprising:
a heat source configured to increase vasodilation in and around a wound area of a patient;
a heat applicator connected to the heat source, the heat applicator comprising:
a heat application layer having an application surface and a heat receiving surface, and a heat conductive layer having a front side and a back side,
wherein the heat conductive layer is made of nanofibers directly affixed to the heat receiving surface of the heat application layer;
a power source connected to the heat source, empowering the heat source, the power source comprising at least one nanotech battery,
wherein the power source and the heat source are integrated into a heat generating body directly affixed to the heat conductive layer of the heat applicator; and
a plurality of flexible lighting mechanisms interwoven with fibers of the heat application layer,
wherein the plurality of flexible lighting mechanisms are light emitting nanofibers having a quantum efficiency of about 0.65 to about 0.95.

2. The treatment device of claim 1, wherein:
the heat applicator is a layered flat structure.

3. The treatment device of claim 1, further comprising:
a control mechanism connected to the power source, the control mechanism being capable of turning on, turning off, and adjusting the output of the power source.

4. The treatment device of claim 1, further comprising:
a non-sticky layer attached to the application surface of the heat application layer.

5. The treatment device of claim 1 wherein the treatment device is a mask.

6. The treatment device of claim 5 wherein the mask further comprises eye slits and breathing slits.

7. The treatment device of claim 1 wherein the treatment device is a stocking for covering the leg and toes.

8. The treatment device of claim 1 wherein the treatment device is a stocking for covering the arm and fingers.

9. The treatment device of claim 1 wherein the treatment device is a wearable cap.

10. The treatment device of claim 1 wherein the treatment device is a cutaneous patch which can be applied to any bodily surface.

11. The treatment device of claim 1 wherein the treatment device may be placed in body cavities.

12. The treatment device of claim 1 wherein the treatment device may be used for the control and extermination of parasites such as lice, bed bugs and dust mites.

13. The treatment device of claim 1 wherein the treatment device is applied to the wound area for at least a first length of time.

14. The treatment device of claim 1 wherein the heat application layer has an adhesive material disposed thereon, the adhesive material being disposed around a periphery of the heat application layer.

15. The treatment device of claim 1 wherein the power source is removably coupled to the heat source.

16. The treatment device of claim 1 wherein the wound area is a wound bed.

17. A wound healing device, consisting of:
 a heat source configured to increase vasodilation in and around a wound area of a patient;
 a heat applicator connected to the heat source, the heat applicator comprising:
  an absorbent heat application layer having an application surface and a heat receiving surface, and a heat conductive layer having a front side and a back side,
   wherein the heat conductive layer is made of nanofibers directly affixed to the heat receiving surface of the heat application layer, and wherein the application surface of the heat application layer has an adhesive material disposed thereon, the adhesive material being covered by a non-sticky layer;
 a power source connected to the heat source, empowering the heat source, the power source comprising at least one nanotech battery,
  wherein the power source and the heat source are integrated into a heat generating body directly attached to the heat applicator,
  wherein the nanotech battery comprises silicon nanowires on a substrate; and
 a plurality of light emitting nanofibers interwoven with fibers of the heat application layer forming a light emitting fabric,
  wherein the plurality of flexible lighting mechanisms are light emitting nanofibers having a quantum efficiency of about 0.65 to about 0.95.

* * * * *